United States Patent [19]

Cocking

[11] Patent Number: 5,126,263

[45] Date of Patent: Jun. 30, 1992

[54] UTILIZATION OF PLANT PROTOPLASTS

[75] Inventor: Edward C. D. Cocking, Woodthorpe, Great Britain

[73] Assignee: University of Nottingham, United Kingdom

[21] Appl. No.: 527,665

[22] Filed: May 24, 1990

Related U.S. Application Data

[63] Continuation of Ser. No. 869,772, Jun. 2, 1986, abandoned.

[30] Foreign Application Priority Data

May 31, 1985 [GB] United Kingdom ............... 8513787

[51] Int. Cl.⁵ .......................... C12N 5/02; C12R 1/41; A61K 37/48; A61K 37/54; A01H 1/00; C05F 11/08

[52] U.S. Cl. ........................... 435/240.47; 435/252.2; 435/878; 424/94.1; 424/94.61; 47/58; 71/7

[58] Field of Search ................ 435/172.2, 240.47, 878, 435/252.2; 47/58; 800/200, 220; 71/7; 424/94.1, 94.61

[56] References Cited

FOREIGN PATENT DOCUMENTS

| | | |
|---|---|---|
| 0114529 | 8/1984 | European Pat. Off. |
| 61162172 | 7/1986 | Japan |
| 1310119 | 3/1973 | United Kingdom |

OTHER PUBLICATIONS

Al-Mallah et al. 1987, Bio/Technol. 5:1319-1322.
Davey et al. (in press) J. Exp. Bot.
Callaham et al. 1981, Can. J. Bot. 59:1647-1664.
Verma et al. 1978, Plant Sci. Lett. 13(2):137-142.
Evans et al. 1983, Int. Rev. Cytol., Suppl. 16:143-159.
Gleba et al. 1984, Monographs on Theor. Appl. Crenet. 8:36-62, Springer-Verlag.
Agrios, G. 1978, Plant pathology, second edition, Academic Press, New York, pp. 52, 210-211.
Ohgawara et al. 1983, Protoplasma 116:145-148.
Paszkowski et al. 1984, Embo J 3:2717-2722.
Gamborg et al. (1981) in Plant Tissue Culture, T. A. Thorpe, ed., Academic Press, N.Y., pp. 115-153.
Bengochea et al. (1986) Plant Protoplasts, Chapman and Hall, New York, pp. 67-76.
Withers et al. (1972) J. Cell Sci 11:59-75.
Evans et al. (1983) in Evans et al., eds., Handbook of Plant Cell Culture, vol. 1, MacMillan Publ. Co., N.Y., pp. 129-130.
M. Frobesher (1962) Fundamentals of Microbiology, Seventh Ed., W. B. Saunders Company, Philadelphia, pp. 497-8.
EC Cocking (1985) Bio/Technology 3:1104-1106.
Evans et al. (1983) in D. A. Evans et al.; eds., Handbook of Plant Cell Culture, vol. 1, MacMillan Publ. Co., N.Y., pp. 124-129.
Davey, M. R. & Cocking, E. C. (1972), Nature 239, 455-456.
Chemical Abstracts 103-67632w (1985).
Lloyd et al., Nature, 305, 311-313 (1983).
Cocking, Biotechnology vol. 3, Dec. 9, 1985 pp. 1104-1106.

Primary Examiner—David T. Fox
Attorney, Agent, or Firm—Sughrue, Mion, Zinn Macpeak & Seas

[57] ABSTRACT

Plant protoplasts are exposed for interaction with an external agent by exposing the plasma membrane of protoplasts in the root hairs of the plant without release of protoplasts from the plant. This may be achieved by enzymatically degrading the plant cell wall at the apices of root hairs under conditions which expose the plasma membrane whilst maintaining or readily permitting restoration of the essential functional integrity of the plant. Enzymatic degradation of the cell wall at the apices of root hairs is possible in a wide range of crop species and other species and to expose the plasma membrane with partial protoplast release. This enables direct interaction with plasmids, viruses and microorganisms at the surface of the plasma membrane of their exposed protoplasts, or the fusion of these with isolated protoplasts of other plant systems.

6 Claims, 1 Drawing Sheet

UTILIZATION OF PLANT PROTOPLASTS

This is a continuation of application Ser. No. 06/869,772 filed Jun. 2, 1986, now abandoned.

FIELD OF THE INVENTION

This invention relates to the biotechnology of plants and more particularly to techniques for the investigation, improvement or modification of plants which entail the use of plant protoplasts.

The use of isolated protoplasts for plant genetic manipulations with the vista of improved crop plants is an increasingly important aspect of plant biotechnology. Whilst the use of protoplasts is highly attractive, it is a distinct disadvantage that they have first to be isolated from plants, subjected to manipulations and then cultured to regenerate whole plants. Indeed for several crop species regenerating plants from protoplasts is still a major barrier to their use for genetic manipulations.

SUMMARY OF THE INVENTION

It is the object of this invention to achieve access to plant protoplasts so that they may be utilised without complete release from the plant.

According to this invention plant protoplasts are exposed for interaction with an external agent by exposing the plasma membrane of protoplasts in the root hairs of the plant without release of protoplasts from the plant. This may be achieved by enzymatically degrading the plant cell wall at the apices of root hairs under conditions which expose the plasma membrane whilst maintaining or readily permitting restoration of the essential functional integrity of the plant.

It has been found possible to achieve enzymatic degradation of the cell wall of the apices of root hairs from a wide range of crop species and other species and to expose the plasma membrane with partial protoplast release. Under suitable conditions root hairs are present on the roots of a wide range of plants, and the ability to remove their apical cell walls at an early stage of development enables direct interaction with plasmids, viruses and micro-organisms at the surface of the plasma membrane of their exposed protoplasts, or the fusion of these with isolated protoplasts of other plant systems. Apart from these more direct consequences for plant genetic manipulations, the ability to expose the plasma membrane of root hairs of legumes will help to elucidate further the plant host factors influencing the interactions of Rhizobia with root hairs which determine legume host specificity. It also provides an opportunity for experimentation to extend legume host range, and also extension to non-legumes, particularly since there is now good evidence that in legumes Rhizobium enzymes provide for degradative penetration of the root hair cell wall. Also, apart from the ability to release subprotoplasts from root hairs for physiological studies, exposure of the plasma membrane of root hairs facilitates further investigations on the presence of plant hormone receptor sites and ionic channels, presently requiring the use of isolated protoplasts. Protoplasts were first isolated enzymatically from plant roots in 1960 (Cocking, E. C., Nature 187, 927-929, 1960) but it is notable that they were not obtained from cells of the more differentiated region of the root tip bearing root hairs.

DESCRIPTION OF THE DRAWINGS

To facilitate an understanding of the present invention the structure of a typical plant root is shown diagrammatically in FIG. 1.

On enlarged scale

Figure 1:
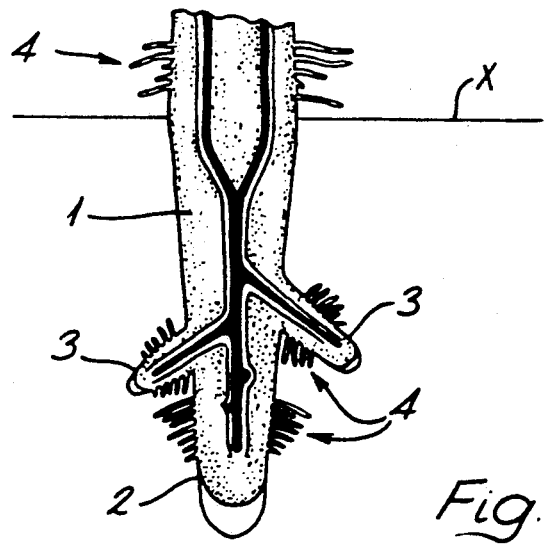
Figure 2:
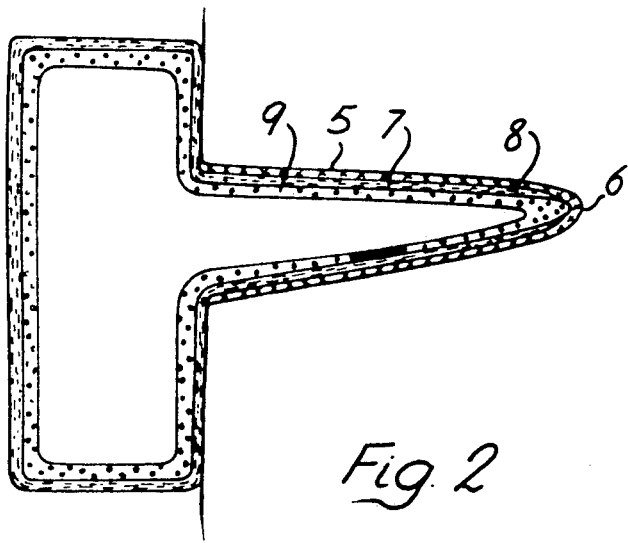
FIG. 2 shows the structure of a root epidermal cell from which the root hair extends.
Figure 3:
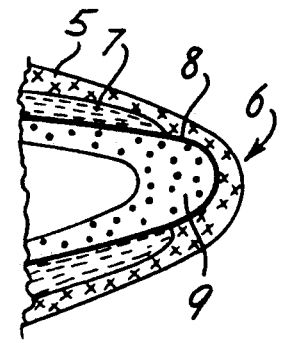
FIG. 3, on more enlarged scale, is a detail of FIG. 2 showing the apex of the root hair.

The plant root below the line X comprises the cortex 1 containing the main root 2 and branch roots 3. Numerous root hairs 4 are shown extending from the epidermis surrounding the cortex 1 both above and below the line X. The line X notionally represents the surface of the medium on which the plant is growing. The root hairs 4 above the line X are therefore aerial hairs.

The wall of the root hair 4 comprises an outermost layer 5 of cellulose microfibrils arranged at random and extending over the hemispherical tip of the root hair at 6, with the extreme tip of the hair being the site of cellulose synthesis. Below the layer 5 there is an inner layer 7 of orientated microfibrils, in which little amorphous material occurs, extending along the cylindrical part of the root hair towards the hemispherical tip 6. Thus except within the extreme tip portion 6, the randomly orientated layer of microfibrils 5 is virtually isolated from the plasma membrane 8 containing the root hair cytoplasm 9.

Figure 4:
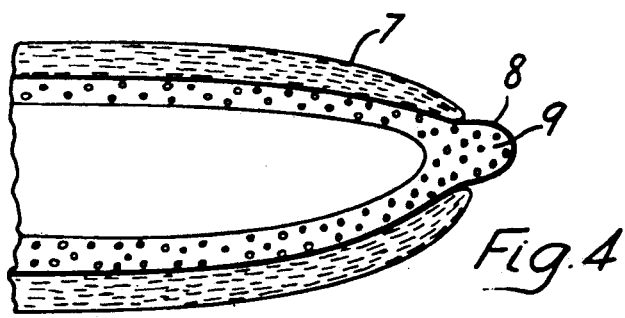
FIGS. 4 and 5 show later developments of the structure shown in FIG. 2.

By careful enzymatic treatment of the root hair region of the plant the random cellulosic layer 5 can be selectively removed whilst the orientated cellulosic layer 7, which is resistant to the enzyme, remains in place. It will thus be appreciated that at the apices of the root hairs the plasma membrane 8 becomes exposed, as seen in FIG. 4, as a result of the specified treatment although the protoplast as a whole remains effectively intact within the root hair and in complete functional association with the plant and all biological processes occurring within it.

DETAILED DESCRIPTION OF THE INVENTION

Figure 5:
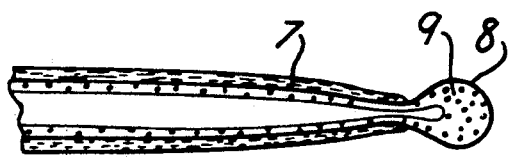

Exposure of the plasma membrane or, in other words, exposure of the protoplast at the apices of root hairs thus provides a port of entry into plant protoplasm for any purpose in accordance with the present invention. The degree of exposure thus obtained may be sufficient for achieving access to the plant interior for the purpose of transport of any desired substance or agent across the plasma membrane. However in order to increase the interface of investigation or treatment of the plant it is preferable to arrange for an osmotic gradient between the plant protoplasm and the external environment in which the plant roots are maintained so as to cause an extrusion of the plasma membrane from the root hair apex such that the result can be described as a partial release of the protoplast. This development is shown in FIG. 5. By controlling the osmotic conditions this partial release can be taken as far as possible without rupture of the membrane. The desired gradient and other conditions of this treatment can readily be determined for any species of plant by prior investigation on experimental samples of specific plant types. For example one method involves the use of aqueous solutions of the appropriate enzyme containing in addition varying concentrations of suitable carbohydrates e.g. sucrose or mannitol which are tested to determine the appropriate concentration of added substance to achieve the desired degree of release of the protoplasts.

For the selective removal of the cell wall cellulose and amorphous material according to this invention many suitable enzymes are available. Cellulase activity is usually sufficient to expose the plasma membrane but pectinase activity is also helpful in achieving the desired effect. Enzymes which have been assessed separately, and in various combinations, include Worthington Cellulase (Freehold, N.J., USA) CEL, a salt free, chromatographically purified cellulase; Cellulysin (Calbiochem, La Jolla, Calif., USA); Cellulase RS and Cellulase RIO (Yakult Honsha Co., Nishinomiya, Japan); Novozyme 234 a multi-enzyme preparation with main activity towards $\beta$-3 linkages (Novo Industries, Bagsvaerd, Denmark); Pectolyase Y23 (Seishim Pharmaceutical, Tokyo, Japan); and Rhozyme HP150 (Rohm & Haas, Philadelphia, USA). The enzymes may conveniently be prepared in Murashige & Skoog's culture medium with added 3% sucrose (MSO) (Physiol. Plant 15, 473-497, 1962). The enzyme solution can be used at a pH of approximately 5.5. Enzyme solutions are filter-sterilised and stored at $-10°$ C. prior to use.

A fluorescent brightening agent, e.g. Tinopal (Ciba Geigy Ltd.) is conveniently used for fluorescence assessments for the presence of cellulose. It may be prepared at the appropriate concentration by dilution with MSO of a saturated solution in water. Roots from seedling of the various crop species, with associated root hairs, can be mounted on slides using cover slip risers as in the microchamber system of Jones et al (American Journal of Botany, 47, 468-470, 1960) and examined either in bright field or with U.V. incident illumination using a Vickers microscope with suitable barrier filters.

The experimental foundation of this invention is illustrated in the following description of representative results obtained.

Roots from turnip seeds germinated in MSO were incubated in 0.001% v/v Tinopal in MSO for 5 minutes, washed in MSO and examined using incident U.V. illumination; they were also examined by bright field illumination. A general fluorescence of cellulose microfibrils over the root hairs of turnip was evident. After placing the Tinopal-treated roots in a solution of 1% (w/v) CEL (Worthington) in MSO in a slide microchamber of the kind referred to above, and incubation at 20° C. for 20 minutes, root hairs still appeared normal, with their cell walls intact, when examined in bright field. But when examined in U.V. the hemispherical tip showed a greatly reduced fluorescence, indicating that most of the randomly orientated cellulose microfibrils at the hemispherical tip of the turnip root hairs had been degraded by the cellulase enzyme preparation. The cellulose at the hemispherical tip is known to be embedded in an amorphous mixture of pectic substances and non-cellulosic polysaccharides, including probably callose ($\beta$1-3 linkages). Assessments were therefore carried out with Pectolyase (a purified pectinase enzyme preparation) and Novo 234 (containing appreciable $\beta$1-3 glucanase and protease activity) added to the CEL enzyme preparation. After treatment with Tinopal turnip roots were incubated, using the slide microchambers, in 1% (w/v) CEL, 0.5% (w/v) Novo 234 and 0.1% (w/v) Pectolyase at 20° C. (Enzyme Mixture, A). After 5 minutes, the tips showed a greatly reduced fluorescence and spherical swellings were visible at the tips of the root hairs. It was clear that part of the protoplast of the root epidermal cell, which extends into the root hair, was being extruded through a break in the cell wall and in this region there was no detectable cellulose using Tinopal. The tips of the rapidly elongating root hairs just beneath the zone of root elongation were very susceptible to cell wall degradation using this enzyme mixture, and most had the cell wall at their tips degraded within 10 minutes with associated protoplast release. Other cell wall degrading enzyme preparations (all in MSO at pH 5.5) were compared using turnip roots. Cellulysin (1% w/v) in place of CEL, and Cellulase RIO (1% w/v) in place of CEL, in Enzyme Mixture A resulted in about 5% of the protoplast release given by Enzyme Mixture A. Cellulase RS (1% w/v) in place of CEL gave about 40% of the release given by Enzyme Mixture A. Cellulase RIO (1% w/v) together with Rhozyme (1% w/v) in place of CEL in this enzyme mixture resulted in about the same release as given by Enzyme Mixture A. Subprotoplasts, sometimes nucleated, could be seen to be progressively extruded from the apices of root hairs, and at an intermediate stage were attached to the main protoplast by a thin protoplasmic strand. If the osmotic pressure of the root hair was nearly equal to that of the medium there was a progressive extrusion of subprotoplasts. If it was suitably greater there was a progressive expansion of the extruding protoplast which sometimes resulted in the protoplast bursting.

Root hairs arise as outgrowths from epidermal cells, and those at a very early stage in their formation (varying in length from slight bulges of the epidermal cells to protuberances up to approximately 50 $\mu$m) had their cell walls very rapidly degraded, within a few minutes, either by Enzyme Mixture A or by this enzyme mixture with the Worthington cellulase replaced by Cellulysin (Enzyme Mixture B), such that the whole of the small emerging root hair became spherical.

Other members of the Cruciferae, cauliflower, oil seed rape and radish have been similarly assessed for protoplast release from their seedling root hairs, and comparable results obtained. Seedlings from representative cereal species of the Gramineae, barley, maize, rice and wheat have also been investigated for the effects of these enzyme mixtures on protoplast release from their root hairs.

Release from root hairs of aerial roots of rice and from barley have been demonstrated, in which there was a progressive expansion of the extruding protoplast. Comparable results were obtained for maize and wheat. In these four Graminaceous species Enzyme Mixture B was more effective than Enzyme Mixture A in releasing protoplasts from the rapidly elongating root hairs just beneath the zone of root elongation; both mixtures were comparably efficacious in degrading of the cell walls of very young root hairs. Protoplast release from root hairs of representative members of the Compositae, lettuce and sunflower was readily achieved in comparable time to members of the Cruciferae using the Enzyme Mixture A. Comparable results were also obtained with this enzyme mixture using roots from seedlings of representative species of the Leguminosae, alfalfa, soybean and white clover; Liliaceae, asparagus and onion; Umbelliferae, carrot; and Roseaceae, strawberry. A selection of Solanaceous crop species, Capsicum, potato, tomato and tobacco, including also *Agrobacterium rhizogenes* induced hairy root cultures of tobacco, gave comparable results when roots were incubated in Enzyme Mixture A.

Growth conditions were standardised to minimise variation in the osmotic pressure of the epidermal and root hair protoplast. In some instances the osmotic pressure of the medium was increased by the addition to the enzyme mixture in MSO of an extra 3% sucrose, if bursting of the protoplast at the tip of the root hair occurred with either of the standard enzyme mixtures. In all the species investigated it was important to avoid plasmolysis of the protoplast within the root hair, otherwise no release of protoplasts took place.

The experimental protocol for exposing plant protoplasts in accordance with the present invention and determining appropriate conditions for utilisation of this effect are further described in the following Examples.

EXAMPLE 1

(1) Seeds are surface sterilised for 20 minutes using 10% Domestos (Lever Bros UK) and then germinated in screw cap jars either on MS medium (Flow Labs Ltd) with 0.9% Agar containing 3% sucrose, (MSO), or on MS medium with 0.9% Agar containing 3% sucrose and 0.1 mg/liter NAA, (MSP2), in the dark at 27° C. (except true potato seed which is germinated at 20° C.).

(2) Rapidly elongating roots approximately 1 cm in length with good root hair development are selected from the seedlings used. The roots with such root hairs are either growing in the agar, in the liquid film of medium on the surface of the agar or as aerial roots in the saturated atmosphere within the jar.

(3) The roots are examined in the slide micro culture chamber. Root hairs are bathed in Enzyme Mixture A either made up in MSO without its usual 3% sucrose, in MSO, or in MSO plus an extra 3% sucrose (i.e. total sucrose is 6%). Within 10 minutes (some root hairs will be affected within 4 minutes) most of the root hairs which are alive and actively elongating will be affected as follows:

(a) Enzyme Mixture A in MSO−3% sucrose

Cell wall at apices of root hairs is degraded and the osmotic pressure of the root hair cell will force the protoplast from the tip of the root hair: it will expand greatly and then burst.

(b) Enzyme Mixture A in MSO

The cell wall at the apex is degraded and the protoplast at the tip is forced out; it expands but usually does not burst.

(c) Enzyme Mixture in MSO+3% sucrose (i.e. plus 6% sucrose in total)

The wall at the apex is degraded. The osmotic pressure of the outside medium prevents more expansion and either the plasma membrane remains just exposed or contracts slightly depending on the exact balance osmotically between the epidermal cell with its root hair and the medium.

With different species these osmotic effects are always observed but the exact level of medium osmotic pressure at which bursting etc. will occur can vary. In the work presented this variation is minimised by germinating seeds in closed jars on MSO or MSP2 (which has the same osmotic pressure as MSO).

The protocol described has been applied to seedlings of the Compositae (Lettuce: *Lactuca sativa* cv. El Toro, sunflower: *Helianthus tuberosus* cv. Giant Yellow), Cruciferae (Cauliflower: *Brassica oleracea* cv. Barrier Reef, oil seed rape: *Brassica napus* cv. Jet Neuf: Radish, *Raphanus sativus* cv. Cherry Belle, turnip: *Brassica rapa* cv. Snowball) Gramineae (barley: *Hordeum vulgare* cv. Aramir, maize: *Zea mays* cv. First of All F1 hybrid, rice: *Oryza sativa*, IR36, wheat: *Triticum aestivum* cv. Broom), Leguminosae (alfalfa: *Medicago sativa* cv. Europe, soybean, *Glycine max* cv. H.P. 2020, white clover: *Trifolium repens* cv. S184), Liliaceae (asparagus: *Asparagus officinalis* cv. Martha Washington, onion: *Allium cepa* cv. Paris silverskin), Rosaceae (strawberry: *Fragaria ananassa* cv. Alexandra). Solanaceae (Capsicum: *Capsicum annuum* cv. Gypsy F1 hybrid, potato: *Solanum tuberosum* true seed reference no. 57207, Thompson and Morgan, Ipswich, tobacco: *Nicotiana tabacum* cv. Xanthi, tomato: *Lycopersicon esculentum* cv. Ailsa Craig) and Umbelliferae (carrot: *Daucus carota* cv. Suko).

EXAMPLE 2

Enzyme Preparations

Preparations having the percentage compositions shown in the following Table vary in potency and range of application. The enzymes are dissolved in MSO medium containing 4 mM morpholine ethane sulphonic acid (MES) buffer pH 5.5–6.5.

| | I | II | III | IV | Observations |
|---|---|---|---|---|---|
| Cellulase R10 | 1 | 1 | 1 | — | I and II are highly potent. I is applicable to dicotyledons. II is applicable to monocotyledons. III and IV are applicable to both monocotyledons and dicotyledons and have a more mild effect on subsequent seedling growth which is desirable. |
| Cellulysin | — | — | 1 | — | |
| Rhozyme | 1 | — | 1 | — | |
| Pectolyase | 0.1 | 0.1 | 0.1 | 0.1 | |
| Novozyme | 0.5 | 0.5 | 0.5 | 0.5 | |
| Worthington CEL | | | | 1 | |

EXAMPLE 3

Effect on Osmoticum

In this example the enzyme preparation used was a modification of preparation IV described in Example 2. In place of MSO the nitrogen-free Fahraeus medium was used (see Example 4) and mannitol was added to the preparations in concentration shown in the Table below.

The root hairs of alfalfa, maize, rice and wheat respond differently to the concentration of mannitol in the enzyme:-

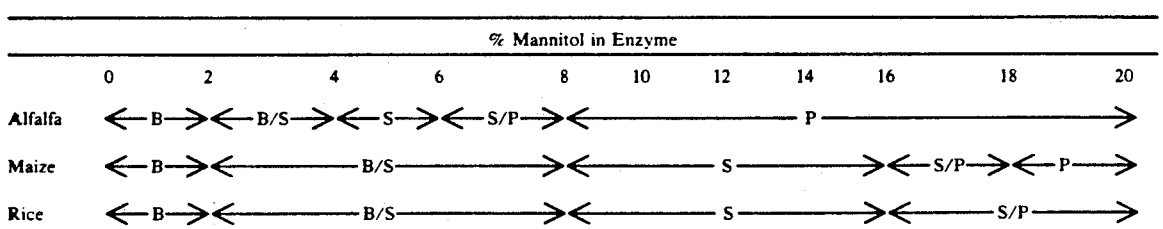

| | % Mannitol in Enzyme | | | |
|---|---|---|---|---|
| Wheat | ←B→ | ←B/S→ | ←S→ | ←S/P→ |

The responses fall into three major zones: bursting of cytoplasm (B), stable subprotoplast release (S) and plasmolysis (P). At some mannitol concentrations a few root hairs may burst and on the same root the others may form stable subprotoplasts. These mannitol concentrations form interzone B/S and likewise there is an interzone S/P.

The root hairs of alfalfa generally form stable protoplasts in enzyme with 4–6% mannitol though there is variation between roots. The monocotyledons maize, rice and wheat form stable root hair subprotoplasts at higher mannitol concentrations (above 8%) and remain stable over a greater concentration range than alfalfa.

The ability to expose the plasma membrane of root hairs of plants using this presently described enzymatic procedure offers many opportunities in plant biotechnology.

1. Uptake of Rhizobia and other Micro-organisms by Root Hairs and the Establishment of Novel Symbiosis This enzymatic procedure for the release of protoplasts enables the uptake of a range of Rhizobium species into root hairs of both legumes and non-legumes.

Rhizobia may be taken up into vesicles by incubation of root hairs with exposed plasma membranes by plasmolysis and treatment with polyethylene glycol following the procedures of Davey, M.R. and Cocking, E.C., (1972), Nature 239, 455–456 and Davey. M. R. and Power, J. B. (1975), Plant Sci. Lett. 5, 269–274, originally introduced for isolated protoplasts. Exposed plasma membrane readily regenerates a new cell wall, Pojnar, E., Willison, J.H.M. and Cocking, E. C. (1967), Protoplasma 64, 460–480. Root hairs with exposed plasma membranes after interaction with Rhizobia may be established in this way. Thus, this uptake of Rhizobia may be used to establish novel nitrogen fixation symbiotic associations, enabling Rhizobia which do not normally form symbiotic associations with certain legumes to do so, and also to form symbiotic associations with non-legumes such as tomato and rice. These applications are not restricted to Rhizobia. Other micro-organisms, such as blue green algae, which often form symbiotic nitrogen fixing associations, and fungi which form mycorrhizal (fungus-root associations) may be similarly taken up into root hairs of a wide range of crop plants. Example 4 below is illustrative of this approach.

EXAMPLE 4

Protocol for Induction of Rhizobium Uptake into Non-Legume Root Hairs

Rice seeds (dehusked) are surface sterilised in 30% (v/v) Domestos solution and germinated on nitrogen-free agar at 28° C. in the dark. This medium (Fahraeus) has the following composition: [$CaCl_2$ (0.1 g), $MgSO_4.7H_2O$ (0.12 g), $KH_2PO_4$ (0.1 g), $Na_2HPO_4.2H_2O$ (0.15 g), Fe citrate (0.005 g), traces of: Mn,Cu,Zn,B,Mo] per liter with 0.8% agar, pH 6.5–7.0.

40–48 hour old seedlings are incubated for 5 minutes in isotonic enzyme mixture of the following composition: [Worthington CEL (1 g), Novozyme 2,3,4 (0.5 g), Pectolyase (0.1 g), mannitol (8.0 g)] per 100 ml, pH 5.6–5.8, then transferred to the Rhizobium uptake treatment.

Exponential phase Rhizobia are harvested by centrifugation and resuspension in fresh yeast extract-mannitol solution (0.5 ml) having the composition [$K_2HPO_4$ (0.5 g), $MgSO_4.7H_2O$ (0.2 g), NaCl (0.1 g), mannitol (10.0 g), yeast extract (Difco) (0.4 g)] per liter, pH 6.8–7.0. Immediately prior to the root immersion this preparation is mixed with 1 ml of polyethylene glycol solution of composition [Polyethylene glycol M.W. 6000 (20.0 g), $CaCl_2.2H_2O$ (0.15 g)] per 100 ml.

The enzyme-treated roots are immersed in the polyethylene glycol with Rhizobia for 5 minutes followed by two washings with mannitol solution [Mannitol (9.0 g) per 100 ml, pH 6.5–7.0].

The seedlings are transferred to nitrogen-free agar in square Petri dishes which can be stacked vertically for optimum seedling growth. All seedlings survive the enzyme treatment although the root growth may be impaired in some cases. Root samples are removed for light and electron microscopic examination.

2. Direct Interaction of Plasmids and Viruses with Whole Plants

Efficient methods for introducing cloned genes into plants are important for their agronomic improvements, and this presently described enzymatic procedure for exposure of the plasma membrane of root hairs of whole plants enables plasmids with a range of cloned genes to be taken up into such enzymatically treated root hairs of a range of crop species. Root hairs with exposed plasma membranes may be incubated with suitable plasmids using a variety of uptake procedures including chemical stimulated uptake (including the use of polyethylene glycol), delivery by encapsulation in liposomes and fusion or plasmid containing bacterial spheroplasts following the procedures described by Freeman et al for plasmid delivery into isolated plant protoplasts (Freeman, J. P., Draper, J., Davey, M. R. Cocking, E. C., Gartland, K.M.W., Harding K. and Pental, D., Plant and Cell Physiology 25, 1353–1365 (1984). Gene transfer using plasmids coupled with the use of electric impulses (8 KV/CM,5 us) as described by Neumann, E., Schaefer-Ridder, M., Wang, Y. and Hofschneider, P. H., EMBO Journal 1, 841–845 (1982) may also be used employed with these enzymatically treated root hairs. Viruses (including DNA containing viruses) may also be transferred into a wide range of crop species using similar uptake procedures.

This methodology is indicated in Example 5 below.

EXAMPLE 5

Protocol for DNA Uptake by Root Hair Protoplasts (a) 2 day old germinating seeds of Oryza sativa are placed in each well of a 5×5 well square Petri plate, arranging the root tips in one corner of the well. The following enzyme preparation (200 μl) is then added.

1% (w/v) Worthington CEL
0.5% (w/v) Novozyme 234
0.1% (w/v) Pectolyase Y23 in the medium of Fahraeus (1957), containing 8% (w/v) mannitol. Incubation proceeds for 10–20 minutes. Fahraeus medium (5 ml) containing 8% (w/v) mannitol is added to each well in order to dilute enzyme and then as much liquid as possible is removed without uncovering the root tips. The dish is sealed and transferred to a 45° C. incubator for 5 minutes. The dish is then transferred to an ice bucket for 1 minute. Plasmid pABD 1, previously linearised by cutting at a unique Sma 1 site, is added to each well, in a volume of 10 μl or less. Polyethylene glycol solution (200 μl of 40% (w/v) PEG 6000 containing 8% (w/v) mannitol) is then added and mixed gently. After incubation for 20 minutes CPW salts medium (6 ml) containing 7.4 g/l calcium chloride, and 8% (w/v) mannitol, is carefully added to each well. The seeds are rested for 30 minutes and then returned to jars of germination medium overnight, prior to selection on an appropriate level of kanamycin, e.g. 400 μg/ml for *Oryza sativa*.

(b) If root hair protoplasts are to be subjected to electrical uptake stimulation, the procedure of (a) is followed except that the step of dilution with Fahraeus medium is carried out at least 3 times, but with 8% (w/v) mannitol containing 0.1% (w/v) morpholinoethane sulphonic acid. Any remaining ions will promote bursting. Also, after the incubation with PEG magnesium chloride is added to a final concentration of 30 mM and electrodes with 0.5 cm electrode gap are inserted into each well, and a potential difference of 400 V applied across the electrodes for three pulses, each of 2 milliseconds. This gives a field strength of 800 V/cm. The method proceeds with the addition of CPW salts medium as in (a).

3. Fusion of Protoplasts Extruding from Root Hair Tips or Isolated from Root Hairs with Protoplasts Isolated from other Plant Species Gene transfer by protoplast fusion is a well established procedure for the transfer of clusters of nuclear or cytoplasmic genes, and the use of protoplasts being released from root hairs now enables the basic strategy of somatic hybridisation to be applied to the intact plant. Such protoplast fusion using either chemical or electrical procedures (Davey, M. R. and Kumar, A., Int. Rev. Cytol. Suppl. 16, 219-299 (1983)) may be used to transfer nuclear genes (controlling for instance symbiotic associations) or cytoplasmic genes (conveying for instance male sterility) without impairment of the functional integrity of the plant. As previously described in 1, exposed plasma membranes readily regenerate a new cell wall and root hairs with exposed plasma membranes, after fusion, may be stabilised in this way. If required, protoplasts can be isolated from root hairs and used for somatic hybridisation by fusion with other isolated protoplasts.

This technique is illustrated in Example 6 below.

EXAMPLE 6

Protocols for Uptake of Rhizobium into Non-Legume Root Hairs

These procedures are generally applicable to all non-legume crop species in which it is possible to achieve enzymatic degradation of the apices of root hairs. The first procedure involves fusion of protoplasts containing Rhizobia (these protoplasts are isolated enzymatically from nodules of the legume) with the exposed plasma membrane of the non-legume root hair whereby the root hair of the non-legume will contain Rhizobia in its cytoplasm. The second procedure involves fusion of protoplasts (subprotoplasts) released from the tips of root hairs of enzymatically-treated root hairs of legumes with the exposed plasma membrane of the non-legume root hair; the hybrid root hair on the non-legume then behaves like a legume root hair and interacts with Rhizobia in the usual way that legumes do during their normal infection with Rhizobia.

PROCEDURE (1)

(a) Rice seeds (or seeds of any other non-legume) are surface sterilised in 30% (v/v) Domestos and germinated on nitrogen-free agar (see Example 4) at 28° C. in the dark, and 2-day-old seedlings are incubated in isotonic enzyme mixture for 5 minutes to expose the plasma membranes at the surface of their root hairs.

(b) Protoplasts are isolated from young nodules of the legume using the procedure described by Davey and Cocking, 1973, Nature, 244, 460, which involves incubating the sliced nodule in a cell wall degrading enzyme mixture in a suitable plasmolyticum. (c) Seedlings of the non-legume following the treatment as detailed in (a) are mixed with nodule protoplasts (which contain Rhizobium) such that the root hairs are mixed with these nodule protoplasts with a ratio of approximately four nodule protoplasts to every root hair. The root hair system of the non-legume with associated isolated root nodule protoplasts is then incubated in autoclaved 30% w/v polyethylene glycol (PEG) M.W. 6000 containing 0.01 $CaCl_2.2H_2O$ and left for 10 minutes at room temperature. The PEG solution is then diluted at 5 minute intervals by the addition of 50% of its volume by nitrogen-free medium (see Example 4, but without agar), and then by the addition of a further 50% of its volume and then by a further 50% of its volume until the PEG has been replaced by this medium. Fusion of the nodule protoplasts with the exposed protoplast of the root hair takes place and will result in the non-legume seedling possessing root hairs containing Rhizobia.

PROCEDURE (2)

(a) The procedure is as in (1)(a).

(b) Subprotoplasts are isolated from root hairs of the legume by treating root hairs of seedlings with the enzyme mixture under conditions which cause extrusion of the protoplast from the root hairs. The subprotoplasts are collected by flotation.

(c) Using PEG as the fusion agent as described in (1) (c) fusion of these root hair subprotoplasts from legumes with the exposed protoplast of the root hair of the non-legume takes place and results in the non-legume seedling possessing root hairs which resemble physiologically (as far as Rhizobium infection is concerned) root hairs of the legume. Such treated seedlings are then incubated with Rhizobia of the required legume specificity for infection of the non-legume to take place.

I claim:

1. A method of exposing the plasma membrane of at least one protoplast in a root hair of a plant for interaction with a plant characteristic modifying external agent, comprising contacting a cell wall of said root hair with a non-natural preparation comprising at least one cell wall degrading enzyme such that said plasma membrane of said protoplast is exposed without releasing said at least one protoplast from said root hair, wherein said exposing is not attributable to the presence of an organism which would naturally cause cell wall degradation of said root hair to expose said plasma membrane.

2. A method according to claim 1, wherein said contacting comprises enzymatically degrading said cell wall at the apex of said root hair.

3. A method according to claim 2, wherein the degree of exposure of said plasma membrane of said at least one protoplast is controlled osmotically.

4. A method for modifying the characteristics of a plant by interaction of at least one plant characteristic modifying external agent with the plasma membrane of at least one protoplast of a root hair of said plant, comprising
   (A) enzymatically degrading a cell wall at an apex of a root hair of said plant to expose said plasma membrane, and
   (B) contacting said at least one plant characteristic modifying external agent with said plasma membrane to produce a modified plant; wherein said degrading is not attributable to the presence of an organism which would naturally cause cell wall degradation of said root hairs to expose said plasma membrane, and wherein said exposing of said plasma membrane of said protoplast allows interaction with said plant characteristic modifying external agent without release of said protoplast from the functionally intact plant.

5. A method for modifying the somatic characteristics of a plant by interaction with at least one protoplast of a root hair of said plant in situ, comprising
   exposing the plasma membrane of said protoplast by applying to said root hair a cell-wall-degrading enzyme to provide an exposed plasma membrane in said root hair and allowing interaction in situ of said exposed plasma membrane with a Rhizobium which does not have a natural nodule-forming association with said plant;
   wherein said exposing of said plasma membrane is not attributable to the presence of an organism which would naturally cause cell wall degradation of said root hair to expose said plasma membrane.

6. A method according to claim 5, wherein the method further comprises establishing a symbiotic association between a Rhizobium organism capable of symbiotic association and said modified plant through proximity of said organism to said exposed plasma membrane.

* * * * *